United States Patent
Mohapatra et al.

(10) Patent No.: US 11,319,297 B2
(45) Date of Patent: May 3, 2022

(54) EFFICIENT AND ENVIRONMENT FRIENDLY PROCESS FOR CHLOROMETHYLATION OF SUBSTITUTED BENZENES

(71) Applicant: ANTHEA AROMATICS PRIVATE LIMITED, Navi Mumbai (IN)

(72) Inventors: Manoj Kumar Mohapatra, Navi Mumbai (IN); Ramamohanrao Bendapudi, Navi Mumbai (IN); Paul Vincent Menacherry, Mumbai (IN); Vincent Paul, Mumbai (IN)

(73) Assignee: ANTHEA AROMATICS PRIVATE LIMITED, Navi Mumbai (IN)

( * ) Notice: Subject to any disclaimer, the term of this patent is extended or adjusted under 35 U.S.C. 154(b) by 0 days.

(21) Appl. No.: 17/419,930

(22) PCT Filed: Jul. 27, 2019

(86) PCT No.: PCT/IB2019/056424
§ 371 (c)(1),
(2) Date: Jun. 30, 2021

(87) PCT Pub. No.: WO2020/250018
PCT Pub. Date: Dec. 17, 2020

(65) Prior Publication Data
US 2022/0081406 A1   Mar. 17, 2022

(30) Foreign Application Priority Data
Jun. 14, 2019 (IN) .............................. 201921023761

(51) Int. Cl.
*C07D 317/54* (2006.01)
*C07C 41/14* (2006.01)
*C07D 317/52* (2006.01)
*C07C 45/51* (2006.01)

(52) U.S. Cl.
CPC ............ *C07D 317/54* (2013.01); *C07C 41/14* (2013.01); *C07C 45/513* (2013.01); *C07D 317/52* (2013.01)

(58) Field of Classification Search
CPC .... C07D 317/54; C07D 317/52; C07C 41/14; C07C 45/513
See application file for complete search history.

(56) References Cited

U.S. PATENT DOCUMENTS

| | | | |
|---|---|---|---|
| 2,219,873 A | 10/1940 | Pinkernelle et al. | |
| 2,485,681 A | 2/1947 | Wachs | |
| 2,447,479 A | 8/1948 | Salt et al. | |
| 2,485,680 A | 10/1949 | Wachs | |
| 2,525,777 A | 10/1950 | Benneville et al. | |
| 2,541,408 A | 2/1951 | Cockerille et al. | |
| 2,569,803 A | 10/1951 | Benneville et al. | |
| 2,596,092 A | 5/1952 | Benneville et al. | |
| 2,676,987 A | 4/1954 | Lewis et al. | |
| 2,846,480 A | 8/1958 | McClaflin et al. | |
| 2,859,253 A | 11/1958 | Snow et al. | |
| 2,878,266 A | 3/1959 | Wachs | |
| 2,945,884 A | 7/1960 | Omietanski et al. | |
| 5,315,018 A | 5/1994 | Penny et al. | |
| 2005/0239841 A1* | 10/2005 | Browning ............ | C07D 409/12 548/364.7 |

FOREIGN PATENT DOCUMENTS

| | | |
|---|---|---|
| CA | 530586 | 9/1956 |
| CA | 684032 | 4/1964 |
| CA | 803 559 | 1/1969 |
| GB | 1026365 | 4/1966 |
| GB | 1067988 | 5/1967 |
| WO | 2016103058 | 6/2016 |

OTHER PUBLICATIONS

Nagasaki et al. Tetrahedron 1992, 48, 797-804 (Year: 1992).*

(Continued)

*Primary Examiner* — Matthew P Coughlin
(74) *Attorney, Agent, or Firm* — Silvia Salvadori

(57) ABSTRACT

Disclosed herein is an efficient, environment friendly and commercially viable process for preparation of chloromethylated compound of formula I in substantially pure form and high yield, from the compound of formula II. The process includes contacting the compound of formula II with a chloromethylating agent generated in-situ by reaction of a formaldehyde precursor and hydrogen chloride, in a suitable solvent/contacting medium and in the presence of a catalytic amount of a short chain/low molecular weight carboxylic acid of formula III. I II III wherein, $R_1$, $R_2$, $R_3$ and $R_4$ are as defined in the description.

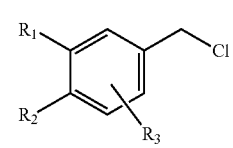

I

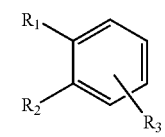

II

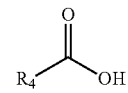

III

14 Claims, No Drawings

(56) References Cited

OTHER PUBLICATIONS

Tohru Kishida et al: "Strong Organic Acids as Efficient Catalysts for the Chloromethylation of m-Xylene: The Synthesis of 1,3-bis (Chloromethyl )-4,6-dimethyl benzene", Industrial & Engineering Chemistry Research, vol. 48, No. 4, Feb. 18, 2009.

International search report issued by the EPO for PCT/IB2015/053112 dated Aug. 31, 2015.

* cited by examiner

EFFICIENT AND ENVIRONMENT FRIENDLY PROCESS FOR CHLOROMETHYLATION OF SUBSTITUTED BENZENES

This application is a U.S. national stage of PCT/IB2019/056424 filed on 27 Jul. 2019 which claims priority to and the benefit of Indian Application No. 20191023761 filed on 14 Jun. 2019 the contents of which are incorporated herein by reference in their entireties.

TECHNICAL FIELD OF THE INVENTION

The present invention pertains to technical field of organic synthesis. In particular, the present invention relates to an efficient, environment friendly and commercially viable process for chloromethylation of substituted benzenes.

BACKGROUND OF THE INVENTION

Chloromethylation is a method of directly substituting a chloromethyl group in an aromatic structure with the elimination of a water molecule. Its importance in synthetic chemistrylies in the versatility of the chloromethyl group to be converted into wide range of other functional groups.

The Blanc chloromethylation of aromatic rings is a versatile method for the synthesis of a variety of fine or specialty chemicals used in various applications such as pharmaceuticals, agrochemicals, dyes, flavours & fragrances, polymers and so on.

The classical chloromethylation reaction is illustrated herein in the following scheme:

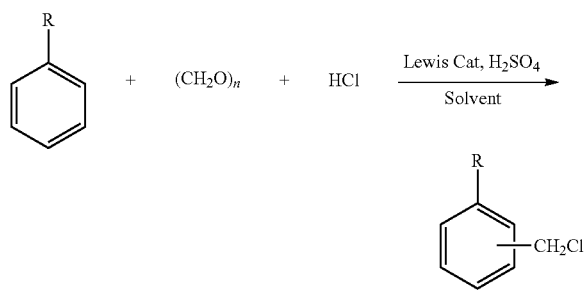

The mechanism of chloromethylation and the reactive species involved have been further elucidated by Olahet. al. [*J. Org. Chem.*, 1981,46, pp 571-577].

Paraformaldehyde (or other suitable polymeric formaldehyde precursor such as 1,3,5-trioxane and the like) and hydrogen chloride are the most common reactants used in the chloromethylation reaction. The conditions vary according to the type of compound to be chloromethylated. In addition to the efficiency of the reaction, the fact that paraformaldehyde and hydrogen chloride are both relatively inexpensive bulk materials, makes the chloromethylation reaction of great industrial importance for the synthesis of several industrially important products such as heliotropin and piperonylbutoxide.

The chloromethyl group, after introduction into the arene ring, can be further functionalized into other groups such as $CH_2OH$, $CH_2OR$, $CH_2OAc$, CHO, $CH_2CN$, $CH_2CO_2H$, $CH_2NH_2$, $CH_2NRR'$ and the like, so that a series of new derivatives can be easily produced (as depicted in Scheme 1), and this type of reaction has been often reported as an early step in a multistepsynthesis of specialty chemicals, e.g. in the manufacture of pharmaceutically active molecules.

Scheme 1

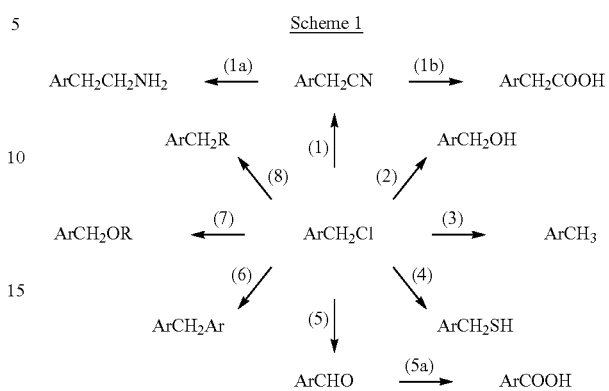

For example, GB786382 discloses a method for chloromethylation employing hydrogen chloride and formaldehyde or paraformaldehyde.

GB1026365 discloses a method for chloromethylation employing paraformaldehyde, acetic acid, hydrochloric acid followed by purging of hydrogen chloride to generate the pressure of about 3 atmospheres. However, the reaction takes a long time and has the additional disadvantage that it needs to be carried out at high temperature.

US2945894 discloses a method for chloromethylation employing paraformaldehyde, concentrated hydrochloric acid, anhydrous zinc chloride and sodium chloride. However this method has the drawback that it generates large quantity of effluent during workup.

U.S. Pat. No. 2,485,680 &U.S. Pat. No. 2,485,681 describe the chloromethylation of dihydrosafrole by mixing and stirring with 40% formaldehyde and concentrated hydrochloric acid at ~20° C. for 36 hours. However, under these conditions, the chloromethylated product is typically accompanied by impurities formed in side reactions.

US2878266 improved the above process by contacting 90% dihydrosafrole, paraformaldehyde, 35% hydrochloric acid and calcium chloride at elevated temperature to obtain the chloromethylated product. However, the drastic conditions employed coupled with the effluent issue make this procedure unattractive for the chloromethylation of substituted benzene compounds which are not stable at higher temperatures under acidic environments, such as alkoxy-, methylenedioxy- and ethylenedioxy-substituted benzene, and so on.

U.S. Pat. No. 2,846,480 describes a process for chloromethylating alkylbenzenes in the presence of sulfuric acid, formaldehyde or its precursor, methanol and phosphorus trichloride. However, the chloromethylated products are obtained after tedious workup and generate huge quantities of effluents.

WO2016/103058A1 discloses a process for the synthesis of alkoxy-substituted benzaldehydes through intermediate preparation of their chloromethylated derivatives from the corresponding alkoxy-substituted benzenes using paraformaldehyde and concentrated hydrochloric acid. However, even though the method disclosed is a straight through procedure for obtaining the desired alkoxybenzaldehydes in substantially pure form and satisfactory yields, the effluent generation issue remains unresolved.

CA684032 discloses a method for chloromethylation of ortho- & para-dichlorobenzenes comprising substituted benzene, concentrated sulfuric acid paraformaldehyde and calcium chloride by contacting at a temperature range of 0-90° C. However, such methods, involving drastic conditions would not be suitable for chloromethylating substrates containing alkoxy/alkylenedioxy benzene ring, besides generating very large quantities of effluent.

GB1067988 discloses a process for chloromethylation comprising reaction of a substituted benzene with anhydrous hydrogen chloride and paraformaldehyde in presence of three-fold excess of anhydrous $ZnCl_2$ and an emulsifier. This process however requires the use of lithium chloride as a co-catalyst and glacial acetic acid as reaction medium and suffers from handling and product separation difficulties.

CA530586 has reported the use of an anhydrous mixture of zinc chloride and a low molecular weight carboxylic acid like acetic or propionic acid for promoting the chloromethylation of aromatic hydrocarbons containing higher alkyl substituents. The preferred ratio of zinc chloride to carboxylic acid in the catalyst mixture reported is one mole of zinc chloride to from two to four moles of the carboxylic acid. Zinc chloride to carboxylic acid ratio lower than 1:1.5 is reported to give incomplete conversion unless excessive amounts of the catalyst mixture are used, leading to excessive effluent generation.

Tohru, Kishida et. al. have observed that strong organic acids such as $CCl_3CO_2H$, $CHCl_2CO_2H$, $CF_3CO_2H$, $CH_3SO_3H$, $CF_3SO_3H$, and PTSA present at approximately 2 to 10 mole %, effectively catalyzed the chloromethylation of m-xylene with hydrochloric acid and trioxane under biphasic conditions [*Ind. Eng. Chem. Res.,* 2009, 48 (4), pp 1831-1839]. However, the use of such strong acids as catalysts would lead to by-product formation during chloromethylation of alkoxy/alkylenedioxy benzenes, besides generating very large quantities of effluent.

From an analysis of the prior art, it is observed that the chloromethylation reaction is typically performed using an excess of concentrated hydrochloric acid and a formaldehyde precursor like paraformaldehyde or trioxane in a chlorinated reaction medium. It has been reported that in the absence of catalyst/promoter, the reactions are usually sluggish but the reaction proceeds with greater ease in presence of Lewis acid catalyst such as zinc chloride, aluminium chloride, stannic chloride, arsenic chloride, boron trifluorideetc (U.S. Pat. Nos. 2,219,873, 2,447,479, 2,525,777, 2,569,803, 2,596,092, 2,676,987, 2,541,408 &U.S. Pat. No. 2,859,253) and/or strong mineral acids such as sulfuric acid. However, the catalysts and reaction media used for this purpose are typically toxic and/or, corrosive, volatile and environmentally hazardous. Additionally, the chloromethylation reaction under these conditions is often accompanied by side-reactions, especially when the substituted benzene compound is not stable at higher temperatures in highly acidic environments. Moreover, the methods disclosed in the prior art also require tedious workups and generates a large quantity of effluents.

In one previously reported method, the chloromethylation is done by reacting paraformaldehyde and hydrogen chloride in acetic acid, however this method requires heating in a closed vessel for longer time, the disadvantage associated with this process is that it proceeds slow requiring time of about 75 hrs to 100 hrs, and may not be suitable for the chloromethylation of aromatic substrates which are not soluble in acetic acid or are unstable in acidic environments.

Moreover, the reactants are typically used in significant excess to complete reaction, which results in formation of di- or tri-chloromethyl derivatives, diarylmethanes, etc., which must be separated by techniques such as distillation, etc. Alternatively, when an excess of the substituted benzene compound is used to reduce the formation of these by products, the excess substrate must be separated to obtain the desired chloromethylated product with better quality profile.

There are many factors that lead to formation of these unwanted by-products.
1) Temperature: Higher temperatures tend to increase by-product formation.
2) Choice of catalyst/promoter: The use of strong acids such as halogen-substituted acetic acids & sulfonic acids for chloromethylating aromatic rings under biphasic conditions. The use of aluminium chloride is known to favour formation of diarylmethane products.
3) Molar ratio and concentration of reagents: In case excess of the substituted benzene substrate is used, a point can be reached where more diarylmethane product will be formed than chloromethylated product if the reaction is allowed to proceed further.

All these factors show how important it is to select the right reaction conditions and catalyst in order to maximize the yield of the chloromethylated product.

The prior art as described herein above does not disclose a satisfactory method for the chloromethylation of substituted alkoxy/alkylenedioxy benzenes devoid of the issues relating to excessive generation of by-products which may necessitate intermediate separation/purification, ease of workup/separation, the minimization of toxic effluents and conforming to the increasing environmental regulations. In view of the above, there is a dire need to develop a process for the preparation of chloromethylated benzene compounds, which is efficient, industrially viable and environment friendly.

The present invention satisfies the existing needs, as well as others, and generally overcomes the deficiencies found in the prior art.

All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

OBJECTS OF THE PRESENT INVENTION

The primary object of the present invention is to provide an efficient, industrially viable and environment friendly process for chloromethylation of substituted benzenes, avoiding the exposure of the substituted benzene substrate to elevated temperature under acidic conditions, thereby obtaining the target aryl methyl chloride compounds in high purity and yield.

A further object of the present invention is to disclose a process for chloromethylation of substituted benzenes, eliminating the use of Lewis acid catalysts and/or strong acids like halosulphonic acid, sulfuric acid, thereby eliminating or minimizing generation of effluent typically associated with conventional chloromethylation processes.

Yet another object of the present invention is to provide a process where the resulting aryl methyl chloride can be further functionalized to desired product(s) without isolation and/or with minimal workup.

Various objects, features, aspects and advantages of the inventive subject matter will become more apparent from the following detailed description of preferred embodiments.

SUMMARY

Aspects of the present invention relate to an efficient, environment friendly and commercially viable process for preparation of a chloromethylated compound of formula I (also referred as aryl methyl chloride) in substantially pure form and high yield, from the corresponding compound of formula II. The process comprises contacting the compound of formula II with a chloromethylating agent generated in-situ by reaction of a formaldehyde precursor and hydrogen chloride, in a suitable solvent/contacting medium and in presence of a catalytic amount of a short chain/low molecular weight carboxylic acid,

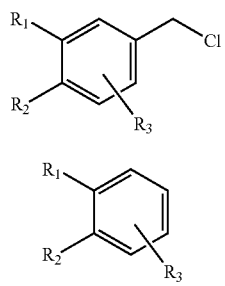

wherein $R_1$, $R_2$ and $R_3$ are independent of each other,
$R_1$ represents H, R or —OR, wherein R is a substituted or unsubstituted $C_1$-$C_4$ alkyl group or substituted or unsubstituted $C_3$-$C_6$ cycloalkyl group;
$R_2$ represents hydroxy group —OH or alkoxy group —OR, wherein R is a substituted or unsubstituted $C_1$-$C_4$ alkyl group or substituted or unsubstituted $C_3$-$C_6$ cycloalkyl group;
or $R_1$ and $R_2$ jointly form an alkylenedioxy group represented by —O—$(CH_2)_n$—O— wherein n is 1, 2 or 3;
$R_3$ is a substituent at any position of the aromatic ring other than position 1, 3 and 4 and represents H, R, —OR, wherein R is a substituted or unsubstituted $C_1$-$C_4$ alkyl group, substituted or unsubstituted $C_3$-$C_6$ cycloalkyl group or SH.

In various embodiments, the process comprises of contacting the substituted benzene of formula II with the chloromethylating agent generated in-situ by reaction of a formaldehyde precursor and hydrogen chloride, in a suitable solvent/contacting medium, and in presence of a catalytic amount of a short chain carboxylic acid of formula III, acting as promoter for said reaction, $$\underset{R_4}{\overset{O}{\underset{\|}{\text{C}}}}\text{OH} \qquad \text{III}$$

wherein $R_4$ represents a alkyl group containing one to six carbon atoms.

The inventive feature of the present invention lies in the fact that the process comprises generating the chloromethylating agent in-situ from a formaldehyde precursor and hydrogen chloride gas in a suitable solvent/contacting medium, which is then reacted with the substituted benzene of formula II in the presence of a catalytic amount of a short chain/low molecular weight carboxylic acid for promoting the chloromethylation reaction, thereby eliminating the use of any Lewis acids such as aluminium chloride, zinc chloride and the like, or strong acids such as sulphuric acid, sulphonic acid and the like, or other salts such as calcium chloride, sodium chloride and the like, as reported in the prior art, which has the benefit of significantly reducing the effluent generated and making the process environmentally friendly.

The said chloromethylation reaction is further characterised by the fact that excess hydrogen chloride can be easily neutralized at the end of the reaction, resulting in a simplified workup with minimum effluent generation, and the resulting aryl methyl chloride with minimal workup can be further functionalized to desired product(s).

According to embodiments of the present invention, the reaction conditions such as reaction temperature, choice of solvent/contacting medium and carboxylic acid of formula III in catalytic amount used as reaction promoter, can be optimised to obtain a high yield of the corresponding chloromethylated product of formula I.

In an aspect, the present invention provides an improved method for carrying out chloromethylation reaction on the substituted benzene compound of formula II, employing relatively non-corrosive catalysts to minimize generation of effluents in workup.

In another aspect, the present invention is directed to the use of low molecular weight carboxylic acid in less than stoichiometric ratio, as catalyst/promoter for the chloromethylation reaction.

In various embodiments, the present invention involves the continuous addition of hydrogen chloride gas to reaction mass comprising the compound of formula II and the chloromethylating agent generated in-situ, to stabilize the chloromethylating agent in presence of water generated in the chloromethylation reaction.

Another aspect of the present invention is directed to simplification of workup and minimization of effluent typically associated with Blanc chloromethylation process.

DETAILED DESCRIPTION OF THE PRESENT INVENTION

The following is a detailed description of the embodiments of the present invention. The embodiments are in such detail as to clearly communicate the disclosure. However, the amount of detail offered is not intended to limit the anticipated variations of embodiments; on the contrary, the intention is to cover all modifications, equivalents, and alternatives falling within the spirit and scope of the present disclosure as defined by the appended claims.

Unless the context requires otherwise, throughout the specification which follow, the word "comprise" and variations thereof, such as, "comprises" and "comprising" are to be construed in an open, inclusive sense that is as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

In some embodiments, the numbers expressing quantities of ingredients, properties such as concentration, process conditions, and so forth, used to describe and claim certain embodiments of the invention are to be understood as being modified in some instances by the term "about." Accordingly, in some embodiments, the numerical parameters set forth in the written description are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable.

The recitation of ranges of values herein is merely intended to serve as a shorthand method of referring individually to each separate value falling within the range. Unless otherwise indicated herein, each individual value is incorporated into the specification as if it were individually recited herein.

All methods described herein can be performed in suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

The headings and abstract of the invention provided herein are for convenience only and do not interpret the scope or meaning of the embodiments.

Various terms are used herein. To the extent a term used in a claim is not defined below, it should be given the broadest definition persons in the pertinent art have given that term as reflected in printed publications and issued patents at the time of filing.

The term "first", "second" and the like, herein do not denote any order, quantity or importance, but rather are used to distinguish one element from another, and the terms "a" and "an" herein do not denote a limitation of quantity, but rather denote the presence of at least one of the referenced items.

The term "contacting" used hereinbefore or hereinafter means reacting, mixing, combining and the like.

In a general embodiment of the present invention, the compound of formula II is contacted with a chloromethylating agent generated in-situ from a formaldehyde precursor and hydrogen chloride, in a suitable solvent/contacting medium and in presence of a catalytic amount of a low molecular weight carboxylic acid of formula III till required conversion of the substituted benzene of formula II into desired product of formula I is achieved,

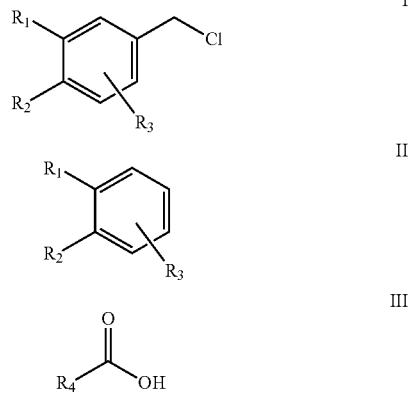

wherein $R_1$, $R_2$ and $R_3$ are independent of each other,
$R_1$ represents H, R or —OR, wherein R is a substituted or unsubstituted $C_1$-$C_4$ alkyl group or substituted or unsubstituted $C_3$-$C_6$ cycloalkyl group;
$R_2$ represents hydroxy group —OH or alkoxy group —OR, wherein R is a substituted or unsubstituted $C_1$-$C_4$ alkyl group or substituted or unsubstituted $C_3$-$C_6$ cycloalkyl group;
or $R_1$ and $R_2$ jointly form an alkylenedioxy group represented by —O—$(CH_2)_n$—O— wherein n is 1, 2 or 3;
$R_3$ is a substituent at any position of the aromatic ring other than position 1, 3 and 4 and represents H, R, —OR, wherein R is a substituted or unsubstituted $C_1$-$C_4$ alkyl group, substituted or unsubstituted $C_3$-$C_6$ cycloalkyl group or SH; and
$R_4$ represents an alkyl group containing one to six carbon atoms.

In many embodiments, the method for chloromethylation as disclosed herein can also be carried out under continuous addition of hydrogen chloride gas, which acts to stabilize the chloromethylating agent in the presence of water generated in the chloromethylation reaction.

In various embodiments, the formaldehyde precursor that can used for the in-situ generation of the chloromethylating agent can be selected from paraformaldehyde and metaformaldehyde (1,3,5-trioxane).

In various embodiments, the solvent/contacting medium can be selected based on its ability to retain the reagents and catalyst/promoter in a single phase to facilitate the reaction. Suitable solvent/contacting medium for the reaction of the compound of formula II with the chloromethylating agent generated in-situ can be selected from the group consisting of chlorinated hydrocarbons, aliphatic hydrocarbons, aromatic hydrocarbons, cyclic hydrocarbons and mixtures thereof.

In one particularly preferred embodiment, the solvent/contacting medium is toluene.

In certain preferred embodiments, the low molecular weight carboxylic acid of formula III represents acetic acid, propionic acid, butanoic acid, pentanoic acid or Hexenoic acid. The catalytic amount of the carboxylic acid of formula III is in a range of from 0.5% to 10% by weight of the compound of formula II.

After the required conversion of the substituted benzene of formula II is achieved, excess hydrogen chloride, if any, can be substantially removed by conventional methods such as purging the reaction medium with nitrogen gas and/or applying vacuum, and any remaining hydrogen chloride can be further neutralized if required, to isolate the chloromethylated compound of formula I in high yield and high purity. In alternative embodiments, the chloromethylated compound of formula I thus obtained can be directly used in further reaction steps without isolation.

The said general embodiment can be depicted as herein below:

1) Contacting paraformaldehyde or other suitable formaldehyde precursor with hydrogen chloride gas in a suitable solvent/contacting medium at a temperature to facilitate in-situ formation of the chloromethylating agent. When the solvent/contacting medium used was toluene, this temperature was typically in the range of from 30° C. to 60° C., and preferably in the range of from 40° C. to 50° C.;
2) Adjusting the temperature of the above mixture to the reaction temperature required for the chloromethylation reaction;
3) Contacting the substituted benzene compound of formula II with the chloromethylating agent generated in-situ in a suitable solvent/contacting medium at a required reaction temperature, in the presence of a catalytic quantity of a low molecular carboxylic acid of formula III acting as catalyst/promoter;
4) Optionally adding excess hydrogen chloride gas during the chloromethylation reaction, if required to stabilize the chloromethylating agent in the presence of water generated in the chloromethylation reaction;
5) Monitoring the progress of the reaction by conventional methods, such as GC, IR, etc, until desired conversion is achieved;
6) Substantially removing excess hydrogen chloride from the reaction mixture by conventional methods, such as purging the reaction medium with nitrogen gas and/or applying vacuum, if required; and
7) Isolating the chloromethyl derivative of formula I in high yield and high purity after conventional work-up techniques such as neutralization of balance hydrogen chloride, aqueous work-up etc., or directly using the chloromethyl derivative of formula I for further reaction without isolation.

It will be understood that the detailed procedure of these embodiments can be varied. Thus, the chloromethylation reaction temperature and/or the ratio of the compound of formula II to the chloromethylating species and/or the quantity of carboxylic acid catalyst may be varied depending on the desired conversion to be achieved, and other polymeric formaldehyde precursors such as 1,3,5-trioxane (metaformaldehyde) may be used instead of paraformaldehyde.

In a specific embodiment of the present invention, this method can be advantageously used to react the compound of the formula II wherein $R_1$ and $R_2$ together jointly form an alkylenedioxy group represented by —O—(CH2)$_n$-O— wherein n is 1, 2 or 3, wherein the alkylenedioxy group is highly susceptible to decomposition at higher temperatures under acidic conditions, to obtain the corresponding chloromethylated compound of formula I in high yield and high purity.

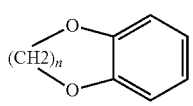 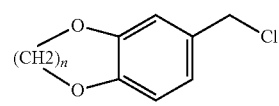

In a further embodiment of the present invention, wherein $R_1$ and $R_2$ together jointly form an alkylenedioxy group represented by —O—(CH2)$_n$-O— wherein n is 1, and $R_3$ is a substituent at the 5$^{th}$ position of aromatic ring and represents H, the substituted benzene compound of formula II is methylene dioxybenzene (1,3-benzodioxole) and the corresponding chloromethylated derivative of formula I (i.e. 5-(chloromethyl)-1,3-benzodioxole) is used as an intermediate in the manufacture of heliotropin, which has wide use in fragrance & flavour applications as well as is a key starting material for pharmaceutical intermediates.

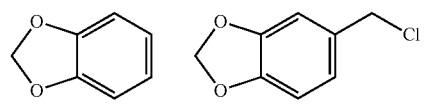

In yet another embodiment of the present invention, wherein $R_1$ and $R_2$ together jointly form an alkylenedioxy group represented by —O—(CH2)$_n$-O— wherein n is 1, and $R_3$ is a substituent at the 5$^{th}$ position of aromatic ring and represents the propyl group, the substituted benzene compound of formula II is dihydrosafrole, and the corresponding chloromethylated derivative of formula I (5-(chloromethyl)-6-propyl-1,3-benzodioxole) is used as an intermediate in the manufacture of piperonylbutoxide, which finds wide application as an insecticide synergist.

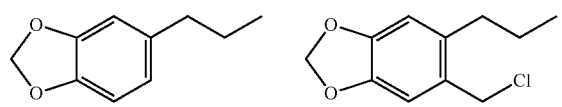

In yet another embodiment of the present invention, wherein $R_1$ and $R_3$=H, and $R_2$=—OCH3, the substituted benzene compound of formula II is anisole, and the corresponding chloromethylated derivative of Formula I (i.e. 4-chloromethyl anisole) can be used as an intermediate in the manufacture of anisaldehyde.

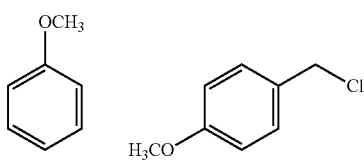 [SMILES: COc1ccccc1 ; COc1ccc(CCl)cc1]

EXAMPLES

The present disclosure is further explained in the form of following examples. However, it is to be understood that the foregoing examples are merely illustrative and are not to be taken as limitations upon the scope of the invention. Various changes and modifications to the disclosed embodiments will be apparent to those skilled in the art. Such changes and modifications may be made without departing from the scope of the invention.

Example-1: Preparation of 5-(Chloromethyl)-1,3-benzodioxole

Toluene (122 g) and Paraformaldehyde (30 g) were charged into a 500 ml reaction flask and the mixture was heated to about 40° C. under stirring and maintained at this temperature under stirring with simultaneous passing of hydrogen chloride gas for about 1 hour, until a clear solution was obtained. The reaction mass was then cooled to about 0° C. and Acetic acid (3.0 g) and Methylene dioxybenzene (122 g) were charged into the reactor under stirring. The reaction mass was then maintained at between 0° C. and 5° C. for 12 hours under stirring with continuous addition of hydrogen chloride gas. The hydrogen chloride addition was stopped and the reaction mass was purged with nitrogen gas for one hour. The reaction mass was washed with water, and the organic layer obtained contained 5-(Chloromethyl)-1,3-benzodioxole ~75.9% and unreacted Methylene dioxybenzene ~19.2% and impurity formation ~5% by GC (excluding solvent).

Example-2: Preparation of 5-(Chloromethyl)-1,3-benzodioxole

Toluene (122 g) and Paraformaldehyde (30 g) were charged into a 500 ml reaction flask and the mixture was heated to about 40° C. under stirring and maintained at this temperature under stirring with simultaneous passing of hydrogen chloride gas for about 1 hour, until a clear solution was obtained. The reaction mass was then cooled to about 0° C. and Acetic acid (6.0 g) and Methylene dioxybenzene (122 g) were charged into the reactor under stirring. The reaction mass was then maintained at between 0° C. and 5° C. for 12 hours under stirring with continuous addition of hydrogen chloride gas. The hydrogen chloride addition was stopped and the reaction mass was purged with nitrogen gas for one hour. The reaction mass was washed with water and the organic layer obtained contained 5-(Chloromethyl)-1,3-benzodioxole ~83.5% and unreacted Methylene dioxybenzene ~9.9% and impurity formation ~6% by GC (excluding solvent).

Example-3: Preparation of 5-(Chloromethyl)-1,3-benzodioxole

Toluene (122 g) and Paraformaldehyde (45 g) were charged into a 500 ml reaction flask and the mixture was heated to about 40° C. under stirring and maintained at this temperature under stirring with simultaneous passing of hydrogen chloride gas for about 1 hour, until a clear solution was obtained. The reaction mass was then cooled to about 5° C. and Acetic acid (12.0 g) and Methylene dioxybenzene (122 g) were charged into the reactor under stirring. The reaction mass was then maintained at between 5° C. and 10° C. for 6 hours under stirring with continuous addition of hydrogen chloride gas. The hydrogen chloride addition was stopped and the reaction mass was purged with nitrogen gas for one hour. The reaction mass was washed with water and the organic layer obtained contained 5-(Chloromethyl)-1,3-benzodioxole ~77.6% and unreacted Methylene dioxybenzene ~18.9% and impurity formation ~4% by GC (excluding solvent).

Example-4: Preparation of 5-(Chloromethyl)-1,3-benzodioxole

Toluene (122 g) and Paraformaldehyde (30 g) were charged into a 500 ml reaction flask and the mixture was heated to about 40° C. under stirring and maintained at this temperature under stirring with simultaneous passing of hydrogen chloride gas for about 1 hour, until a clear solution was obtained. The reaction mass was then cooled to about 0° C. and Propionic acid (7.4 g) and Methylene dioxybenzene (122 g) were charged into the reactor under stirring. The reaction mass was then maintained at between 0° C. and 5° C. for 12 hours under stirring with continuous addition of hydrogen chloride gas. The hydrogen chloride addition was stopped and the reaction mass was purged with nitrogen gas for one hour. The reaction mass was washed with water and the organic layer obtained contained 5-(Chloromethyl)-1,3-benzodioxole ~85.2% and unreacted Methylene dioxybenzene ~11.6% and impurity formation ~3% by GC (excluding solvent).

Example-5: Preparation of 5-(Chloromethyl)-1,3-benzodioxole

Toluene (122 g) and Paraformaldehyde (30 g) were charged into a 500 ml reaction flask and the mixture was heated to about 40° C. under stirring and maintained at this temperature under stirring with simultaneous passing of hydrogen chloride gas for about 1 hour, until a clear solution was obtained. The reaction mass was then cooled to about 0° C. and Hexanoic acid (6.0 g) and Methylene dioxybenzene (122 g) were charged into the reactor under stirring. The reaction mass was then maintained at between 0° C. and 5° C. for 11 hours under stirring with continuous addition of hydrogen chloride gas. The hydrogen chloride addition was stopped and the reaction mass was purged with nitrogen gas for one hour. The reaction mass was washed with water and the organic layer obtained contained 5-(Chloromethyl)-1,3-benzodioxole ~75.3% and unreacted Methylene dioxybenzene ~18.5% and impurity formation ~6% by GC (excluding solvent).

Example-6: Preparation of 5-(Chloromethyl)-1,3-benzodioxole (without Carboxylic Acid Catalyst)

Toluene (122 g) and Paraformaldehyde (30 g) were charged into a 500 ml reaction flask and the mixture was heated to about 40° C. under stirring and maintained at this temperature under stirring with simultaneous passing of hydrogen chloride gas for about 1 hour, until a clear solution was obtained. The reaction mass was then cooled to about 0° C. and Methylene dioxybenzene (122 g) were charged into the reactor under stirring. The reaction mass was then maintained at between 0° C. and 5° C. for 12 hours under stirring with continuous addition of hydrogen chloride gas. The hydrogen chloride addition was stopped and the reaction mass was purged with nitrogen gas for one hour. The reaction mass was washed with water and the organic layer obtained contained 5-(Chloromethyl)-1,3-benzodioxole ~73.2% and unreacted Methylene dioxybenzene ~19.6% and impurity formation ~7% by GC (excluding solvent).

Example-7: Preparation of 5-(Chloromethyl)-1,3-benzodioxole

Toluene (122 g) and Paraformaldehyde (30 g) were charged into a 500 ml reaction flask and the mixture was heated to about 40° C. under stirring and maintained at this temperature under stirring with simultaneous passing of hydrogen chloride gas for about 1 hour, until a clear solution was obtained. The reaction mass was then cooled to about 0° C. and Formic acid (6.0 g) and Methylene dioxybenzene (122 g) were charged into the reactor under stirring. The reaction mass was then maintained at between 0° C. and 5° C. for 10 hours under stirring with continuous addition of hydrogen chloride gas. The hydrogen chloride addition was stopped and the reaction mass was purged with nitrogen gas for one hour. The reaction mass was washed with water and the organic layer obtained contained 5-(Chloromethyl)-1,3-benzodioxole ~52.2% and unreacted Methylene dioxybenzene ~33.3% and impurity formation ~15% by GC (excluding solvent).

Example-8: Preparation of 5-(Chloromethyl)-1,3-benzodioxole

Toluene (122 g) and Paraformaldehyde (15 g) were charged into a 500 ml reaction flask and the mixture was heated to about 40° C. under stirring and maintained at this temperature under stirring with simultaneous passing of hydrogen chloride gas for about 1 hour, until a clear solution was obtained. The reaction mass was then cooled to about 5° C. and Acetic acid (6.0 g) and Methylene dioxybenzene (122 g) were charged into the reactor under stirring. The reaction mass was then maintained at between 5° C. and 6° C. for 6 hours under stirring with continuous addition of hydrogen chloride gas. The hydrogen chloride addition was stopped and the reaction mass was purged with nitrogen gas for one hour. The reaction mass was washed with water and the organic layer obtained contained 5-(Chloromethyl)-1,3-benzodioxole ~40.8% and unreacted Methylene dioxybenzene ~56.6% and impurity formation ~3% by GC (excluding solvent).

Example-9: Preparation of 5-(Chloromethyl)-1,3-benzodioxole

Toluene (122 g) and Paraformaldehyde (30 g) were charged into a 500 ml reaction flask and the mixture was heated to about 40° C. under stirring and maintained at this temperature under stirring with simultaneous passing of hydrogen chloride gas for about 1 hour, until a clear solution was obtained. The reaction mass was then cooled to about 5° C. and Acetic acid (6.0 g) and Methylene dioxybenzene (122 g) were charged into the reactor under stirring. The reaction mass was then maintained at between 5° C. and 10° C. for 8 hours under stirring with continuous addition of hydrogen chloride gas. The hydrogen chloride addition was stopped and the reaction mass was purged with nitrogen gas for one hour. The reaction mass was washed with water and the organic layer obtained contained 5-(Chloromethyl)-1,3-benzodioxole ~74.4% and unreacted Methylene dioxybenzene ~20% and impurity formation ~5% by GC (excluding solvent).

Example-10: Preparation of Heliotropin

Toluene (122 g) and Paraformaldehyde (45 g) were charged into a 500 ml reaction flask and the mixture was heated to about 40° C. under stirring and maintained at this temperature under stirring with simultaneous passing of hydrogen chloride gas for about 1 hour, until a clear solution was obtained. The reaction mass was then cooled to about 5° C. and Acetic acid (6.0 g) and Methylene dioxybenzene (122 g) were charged into the reactor under stirring. The reaction mass was then maintained at between 5° C. and 6° C. for 6 hours under stirring with continuous addition of hydrogen chloride gas. The hydrogen chloride addition was stopped and the reaction mass was purged with nitrogen gas for one hour. At the end of the reaction the organic layer contained 5-(Chloromethyl)-1,3-benzodioxole ~82.1% and unreacted Methylene dioxybenzene ~13.5% and impurity formation ~4% by GC (excluding solvent). 150 g of Hexamine was added under stirring and the temperature of the reaction mass was increased to about 80° C. and maintained at this temperature under stirring for about 4 hour, till the content of the chloromethyl derivative was less than 0.5% by GC analysis. 360 g of 50% aqueous acetic acid was added to the resulting hexamine complex and the reaction mass was digested at about 90° C. for about 6 hours. After completion of the reaction, the reaction mass was diluted with water to separate the organic layer, and product and unreacted Methylene dioxybenzene was further extracted from the aqueous layer using Toluene. The organic layer together with the Toluene extracts was distilled to separate a fraction containing unreacted 19 g of Methylene dioxybenzene and 91 g of Heliotropin (GC purity >98%, yield 88.3% w/w on Methylene dioxybenzene consumed).

Example-11: Preparation of Heliotropin

Toluene (122 g) and Paraformaldehyde (60 g) were charged into a 500 ml reaction flask and the mixture was heated to about 40° C. under stirring and maintained at this temperature under stirring with simultaneous passing of hydrogen chloride gas for about 1 hour, until a clear solution was obtained. The reaction mass was then cooled to about 5° C. and Acetic acid (6.0 g) and Methylene dioxybenzene (122 g) were charged into the reactor under stirring. The reaction mass was then maintained at between 5° C. and 10° C. for 6 hours under stirring with continuous addition of hydrogen chloride gas. The hydrogen chloride addition was stopped and the reaction mass was purged with nitrogen gas for one hour. At the end of the reaction the organic layer contained 5-(Chloromethyl)-1,3-benzodioxole ~87.7% and unreacted Methylene dioxybenzene ~6.7% and impurity formation ~5% by GC (excluding solvent). 150 g of Hexamine was added under stirring and the temperature of the reaction mass was increased to about 80° C. and maintained at this temperature under stirring for about 4 hour, till the content of the chloromethyl derivative was less than 0.5% by GC analysis. 360 g of 50% aqueous acetic acid was added to the resulting hexamine complex and the reaction mass was digested at about 90° C. for about 6 hours. After completion of the reaction, the reaction mass was diluted with water to separate the organic layer, and product and unreacted Methylene dioxybenzene was further extracted from the aqueous layer using Toluene. The organic layer together with the Toluene extracts was distilled to separate a fraction containing unreacted 16 g of Methylene dioxybenzene and 91 g of Heliotropin (GC purity >98%, yield 85.8% w/w on Methylene dioxybenzene consumed).

Example-12: Preparation of Piperonyl Butoxide

Toluene (122 g) and Paraformaldehyde (45 g) were charged into a 500 ml reaction flask and the mixture was heated to about 40° C. under stirring and maintained at this temperature under stirring with simultaneous passing of hydrogen chloride gas for about 1 hour, until a clear solution was obtained. The reaction mass was then cooled to about 15° C. and Acetic acid (6.0 g) and Dihydrosafrole (164 g) were charged into the reactor under stirring. The reaction mass was then maintained at between 15° C. and 20° C. for 6 hours under stirring with continuous addition of hydrogen chloride gas. The hydrogen chloride addition was stopped and the reaction mass was purged with nitrogen gas for one hour. The hydrogen chloride addition was stopped and the reaction mass was purged with nitrogen gas for one hour. The reaction mass was washed with water and the organic layer obtained contained 5-(Chloromethyl)-6-propyl-1,3- benzodioxole ~79.0% and unreacted Dihydrosafrole 11.0% (excluding solvent). This was reacted with butyl carbitol (178 g) and sodium hydroxide (60.0 g) at 30° C. for 5 hours under stirring. After completion of the reaction, the reaction mass was diluted with water to separate the organic layer. The organic layer was distilled to separate a fraction containing unreacted 20 g of Dihydrosafrole and 230 g of Piperonyl Butoxide (GC purity >96%, yield 159.7% w/w on Dihydrosafrole consumed).

Example-13: Preparation of Chloromethyl Anisole

Hexane (122 g) and Paraformaldehyde (45 g) were charged into a 500 ml reaction flask and the mixture was heated to about 40° C. under stirring and maintained at this temperature under stirring with simultaneous passing of hydrogen chloride gas for about 1 hour, until a clear solution was obtained. The reaction mass was then cooled to about 15° C. and Acetic acid (6.0 g) and Anisole (108 g) were charged into the reactor under stirring. The reaction mass was then maintained at between 15° C. and 20° C. for 5 hours under stirring with continuous addition of hydrogen chloride gas. The hydrogen chloride addition was stopped and the reaction mass was purged with nitrogen gas for one hour. The reaction mass was washed with water and the organic layer obtained contained 4-(Chloromethyl)-anisole ~58.5%, 2-(Chloromethyl)-anisole ~19.8% and unreacted anisole ~2.3%.

Example-14: Preparation of Chloromethyl Anisole

Cyclohexane (122 g) and Paraformaldehyde (45 g) were charged into a 500 ml reaction flask and the mixture was heated to about 40° C. under stirring and maintained at this temperature under stirring with simultaneous passing of hydrogen chloride gas for about 1 hour, until a clear solution was obtained. The reaction mass was then cooled to about 15° C. and Acetic acid (6.0 g) and Anisole (108 g) were charged into the reactor under stirring. The reaction mass was then maintained at between 15° C. and 20° C. for 5 hours under stirring with continuous addition of hydrogen chloride gas. The hydrogen chloride addition was stopped and the reaction mass was purged with nitrogen gas for one hour. The reaction mass was washed with water and the organic layer obtained contained 4-(Chloromethyl)-anisole ~60.5%, 2-(Chloromethyl)-anisole ~20.8% and unreacted anisole ~6.8%.

Example-15: Preparation of 4-Anisaldehyde

Toluene (122 g) and Paraformaldehyde (45 g) were charged into a 500 ml reaction flask and the mixture was heated to about 40° C. under stirring and maintained at this temperature under stirring with simultaneous passing of hydrogen chloride gas for about 1 hour, until a clear solution was obtained. The reaction mass was then cooled to about 15° C. and Acetic acid (6.0 g) and Anisole (108 g) were charged into the reactor under stirring. The reaction mass was then maintained at between 15° C. and 20° C. for 5 hours under stirring with continuous addition of hydrogen chloride gas. The hydrogen chloride addition was stopped and the reaction mass was purged with nitrogen gas for one hour. At the end of the reaction the organic layer contained 4-(Chloromethyl)-anisole ~64.1%, 2-(Chloromethyl)-anisole ~20.3% and unreacted anisole ~5.2%. 150 g of Hexamine was added under stirring and the temperature of the reaction mass was increased to about 80° C. and maintained at this temperature under stirring for about 4 hour, till the content of the chloromethyl derivative was less than 0.5% by GC analysis. 360 g of 50% aqueous acetic acid was added to the resulting hexamine complex and the reaction mass was digested at about 90° C. for about 6 hours. After completion of the reaction, the reaction mass was diluted with water to separate the organic layer, and product and unreacted anisole was further extracted from the aqueous layer using Toluene. The organic layer together with the Toluene extracts was distilled to separate a fraction containing unreacted 10 g of Anisole and 75 g of Anisaldehyde (GC purity >98% (sum of both isomers), yield 76.5% w/w on Anisole consumed).

Example-16: Preparation of 4-(Chloromethyl)-1,2-dimethoxybenzene

Toluene (122 g) and Paraformaldehyde (30 g) were charged into a 500 ml reaction flask and the mixture was heated to about 40° C. under stirring and maintained at this temperature under stirring with simultaneous passing of hydrogen chloride gas for about 1 hour, until a clear solution was obtained. The reaction mass was then cooled to about 15° C. and Acetic acid (6.0 g) and 1,2-Dimethoxybenzene (138 g) were charged into the reactor under stirring. The reaction mass was then maintained at between 15° C. and 20° C. for 6 hours under stirring with continuous addition of hydrogen chloride gas. The hydrogen chloride addition was stopped and the reaction mass was purged with nitrogen gas for one hour. The reaction mass was washed with water and the organic layer obtained contained 4-(Chloromethyl)-1,2-dimethoxybenzene ~57.0% and unreacted 1,2-Dimethoxybenzene ~27.1%.

The above Examples are further summarized in table-1 below:

TABLE 1

| Example No. | Substrate | Qty (g) | Carboxylic Acid | Qty (g) | Mole per mole of substrate | Paraformaldehyde (g) | Mole per mole of substrate | Solvent | Temp (° C.) | Time (h) | Product | Product (GC %) | Substrate (GC %) |
|---|---|---|---|---|---|---|---|---|---|---|---|---|---|
| 1 | MDB | 122 | Acetic Acid | 3 | 0.05 | 30 | 1.0 | Toluene | 0 to 5 | 12 | 5-(Chloromethyl)-1,3-benzodioxole | 75.9 | 19.2 |
| 2 | MDB | 122 | Acetic Acid | 6 | 0.10 | 30 | 1.0 | Toluene | 0 to 5 | 12 | 5-(Chloromethyl)-1,3-benzodioxole | 83.5 | 9.9 |
| 3 | MDB | 122 | Acetic Acid | 12 | 0.20 | 45 | 1.5 | Toluene | 5 to 10 | 6 | 5-(Chloromethyl)-1,3-benzodioxole | 77.6 | 18.9 |
| 4 | MDB | 122 | Propionic Acid | 7.4 | 0.10 | 30 | 1.0 | Toluene | 0 to 5 | 12 | 5-(Chloromethyl)-1,3-benzodioxole | 85.2 | 11.6 |
| 5 | MDB | 122 | Hexanoic acid | 6 | 0.05 | 30 | 1.0 | Toluene | 0 to 5 | 11 | 5-(Chloromethyl)-1,3-benzodioxole | 75.3 | 18.5 |

TABLE 1-continued

| Example No. | Substrate | Qty (g) | Carboxylic Acid | Qty (g) | Mole per mole of substrate | Paraformaldehyde (g) | Mole per mole of substrate | Solvent | Temp (° C.) | Time (h) | Product | Product (GC %) | Substrate (GC %) |
|---|---|---|---|---|---|---|---|---|---|---|---|---|---|
| 6 | MDB | 122 | — | 0 | 0.00 | 30 | 1.0 | Toluene | 0 to 5 | 12 | 5-(Chloromethyl)-1,3-benzodioxole | 73.2 | 19.6 |
| 7 | MDB | 122 | Formic acid | 6 | 0.13 | 30 | 1.0 | Toluene | 0 to 5 | 10 | 5-(Chloromethyl)-1,3-benzodioxole | 52.2 | 33.0 |
| 8 | MDB | 122 | Acetic Acid | 6 | 0.10 | 15 | 0.5 | Toluene | 5 to 10 | 6 | 5-(Chloromethyl)-1,3-benzodioxole | 40.8 | 56.6 |
| 9 | MDB | 122 | Acetic Acid | 6 | 0.10 | 30 | 1.0 | Toluene | 5 to 10 | 8 | 5-(Chloromethyl)-1,3-benzodioxole | 74.4 | 20.0 |
| 10 | MDB | 122 | Acetic Acid | 6 | 0.10 | 45 | 1.5 | Toluene | 5 to 10 | 6 | 5-(Chloromethyl)-1,3-benzodioxole | 82.1 | 13.5 |
| 11 | MDB | 122 | Acetic Acid | 6 | 0.10 | 60 | 2.0 | Toluene | 5 to 10 | 6 | 5-(Chloromethyl)-1,3-benzodioxole | 87.7 | 6.7 |
| 12 | DHS | 164 | Acetic Acid | 6 | 0.10 | 45 | 1.5 | Toluene | 15 to 20 | 6 | 5-(Chloromethyl)-6-propyl-1,3-benzodioxole | 79.0 | 11.0 |
| 13 | Anisole | 108 | Acetic Acid | 6 | 0.10 | 45 | 1.5 | Hexane | 15 to 20 | 5 | 2 & 4-(Chloromethyl) anisole | 19.8/58.5 | 2.3 |
| 14 | Anisole | 108 | Acetic Acid | 6 | 0.10 | 45 | 1.5 | Cyclohexane | 15 to 20 | 5 | 2 & 4-(Chloromethyl) anisole | 20.8/60.5 | 6.8 |
| 15 | Anisole | 108 | Acetic Acid | 6 | 0.10 | 45 | 1.5 | Toluene | 15 to 20 | 5 | 2 & 4-(Chloromethyl) anisole | 20.3/64.1 | 5.2 |
| 16 | 1,2-DMB | 138 | Acetic Acid | 6 | 0.10 | 30 | 1.0 | Toluene | 15 to 20 | 6 | 4-(Chloromethyl)-1,2-dimethoxybenzene | 57.0 | 27.1 |

TECHNICAL ADVANTAGE OF THE PRESENT INVENTION

The inventors of present invention have herein provided a solution to the shortcomings of the prior art by developing an efficient process for carrying out the said reaction comprising the in-situ generation of the chloromethylating agent in a suitable solvent by the reaction of hydrogen chloride with a formaldehyde precursor, and carrying out the chloromethylation reaction in the presence of a catalytic amount of low molecular weight carboxylic acid which acts as a catalyst/promoter of the reaction.

The inventors of the present invention have provided a solution wherein the chloromethylating agent is generated in-situ by passing hydrogen chloride gas into a mixture of paraformaldehyde and the solvent/contacting medium at a temperature typically in the range 30° C. to 50° C., and the reaction mass is then adjusted to the reaction temperature required for carrying out the chloromethylation reaction, which is typically lower than the above temperature range, before the addition of the substituted benzene compound of formula II. In this way the inventors of the present invention have provided a method to limit the exposure of the substituted benzene compound to higher temperatures, thereby minimising the formation of by-products, and obtaining the target aryl methyl chloride compound of formula I in high yield and purity.

The inventors of the present invention have observed that chloromethylation of substituted benzene by the reaction with the chloromethylating agent generated in-situ is accelerated in the presence of short chain/low molecular weight carboxylic acid present in catalytic quantities. Although the prior art discloses use of anhydrous mixture of zinc chloride in combination with low molecular weight carboxylic acid like acetic or propionic acid is extremely active in promoting the chloromethylation, the ratio of zinc chloride and carboxylic acid used was very high, typically in the range 1:2 to 4 moles of zinc chloride to carboxylic acid). Moreover, none of the prior art teach the standalone use of carboxylic acids such as acetic acid, present in catalytic quantities acting as catalyst/promoter to accelerate the chloromethylation reaction in the absence of the Lewis acid.

The inventors of the present invention have also observed that after completion of the chloromethylation reaction, the excess hydrogen chloride can be substantially removed by conventional methods such as purging the reaction medium with nitrogen gas and/or applying vacuum, and the remaining hydrogen chloride can be further neutralized if required, resulting in a clean and simple workup with minimum effluent generation, and the resulting aryl methyl chloride with minimal workup can be further functionalized to the desired product(s).

For example, after carrying out the chloromethylation of methylene dioxybenzene, the excess hydrogen chloride can be substantially removed by purging the reaction medium with nitrogen gas, and the chloromethyl species without isolation can be converted to the target compound heliotropin by proceeding for the Sommlet reaction without workup and generation of any liquid effluent in the chloromethylation step.

The advantages of the present invention over the prior art may be summarized as follows:

1) The process of the present invention uses catalytic quantity of low molecular weight carboxylic acid, and eliminates the use of Lewis acids and/or mineral acids such as sulfuric acid, thereby minimising effluent problems and making the process industrially viable and environmentally friendly.
2) The process of the present invention avoids biphasic reaction typically associated with the Blanc reaction by carrying out the reaction in a solvent/contacting medium suitable for the in-situ generation of the chloromethylating agent and the subsequent reaction with the substituted benzene substrate.

3) The process of the invention can be carried out without the chlorinated solvents typically used for chloromethylation reaction and without usage of the conventional halomethylation catalysts.

4) The chloromethylation reaction can be carried out at relatively low temperatures thereby minimizing the decomposition of the substituted benzene compounds at high temperatures under acidic conditions, and obtaining the target aryl methyl chloride compound of Formula I in high purity and yield.

5) The process of the present invention provides for easy work up and high purity and yield of the chloromethylated product. The excess hydrogen chloride can be substantially removed by conventional methods such as purging the reaction medium with nitrogen gas and/or applying vacuum, and the remaining hydrogen chloride can be further neutralized if required, resulting in a clean and simple workup with minimum effluent generation, and the resulting aryl methyl chloride without isolation and/or with minimal workup can be further functionalized to the desired product (s).

In view of the above, the present invention provides a novel method for chloromethylation of the substituted benzene in high purity and yield, while minimizing the generation of large quantities of effluent typically associated with this reaction.

The method disclosed in the present invention may be advantageously used for the industrial manufacture of several industrially important products such as heliotropin (from 5-(chloromethyl)-1,3-benzodioxole), piperonylbutoxide (from 5-(chloromethyl)-6-propyl-1,3-benzodioxole) and anisaldehyde (from 4-chloromethyl anisole), among others.

We claim:

1. A process for preparing a compound of formula I, comprising contacting a compound of formula II with a chloromethylating agent generated in-situ by reaction of a formaldehyde precursor and hydrogen chloride, in a solvent and in presence of a catalytic amount of a carboxylic acid of formula III,

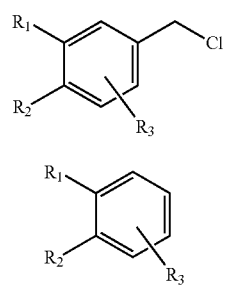

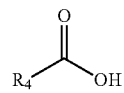

wherein $R_1$, $R_2$ and $R_3$ are independent of each other,
$R_1$ represents H, R or —OR, wherein R is a substituted or unsubstituted $C_1$-$C_4$ alkyl group or substituted or unsubstituted $C_3$-$C_6$ cycloalkyl group;
$R_2$ represents hydroxy group —OH or alkoxy group —OR, wherein R is a substituted or unsubstituted $C_1$-$C_4$ alkyl group or substituted or unsubstituted $C_3$-$C_6$ cycloalkyl group;
or $R_1$ and $R_2$ jointly form an alkylenedioxy group represented by —O—$(CH_2)_n$—O— wherein n is 1, 2 or 3;
$R_3$ is a substituent at any position of the aromatic ring other than position 1, 3 and 4 and represents H, R, —OR, wherein R is a substituted or unsubstituted $C_1$-$C_4$ alkyl group, substituted or unsubstituted $C_3$-$C_6$ cycloalkyl group or SH; and
$R_4$ represents an alkyl group containing one to six carbon atoms;
wherein the catalytic amount of the carboxylic acid of formula III is in a range of from 0.5% to 10% by weight of the compound of formula II.

2. The process as claimed in claim 1, wherein the formaldehyde precursor is paraformaldehyde.

3. The process as claimed in claim 1, wherein the formaldehyde precursor is metaformaldehyde.

4. The process as claimed in claim 1, wherein the solvent is selected from the group consisting of chlorinated hydrocarbons, aliphatic hydrocarbons, aromatic hydrocarbons, cyclic hydrocarbons and mixtures thereof.

5. The process as claimed in claim 1, wherein the solvent is toluene.

6. The process as claimed in claim 1, wherein the compound of formula II and the chloromethylating agent are contacted in presence of hydrogen chloride gas.

7. The process as claimed in claim 1, wherein the carboxylic acid is acetic acid.

8. The process as claimed in claim 1, wherein the carboxylic acid is propionic acid.

9. The process as claimed in claim 1, wherein the compound of formula II is 1,3-benzodioxole and the corresponding compound of formula I is 5-(chloromethyl)-1,3-benzodioxole.

10. The process as claimed in claim 9, wherein the 5-(chloromethyl)-1,3-benzodioxole is further converted to heliotropin.

11. The process as claimed in claim 1, wherein the compound of formula II is dihydrosafrole and the corresponding compound of formula I is 5-(chloromethyl)-6-propyl-1,3-benzodioxole.

12. The process as claimed in claim 11, wherein the 5-(chloromethyl)-6-propyl-1,3-benzodioxole is further converted to piperonylbutoxide.

13. The process of as claimed in claim 1, wherein the compound of formula II is anisole and the corresponding compound of formula I is 4-chloromethyl anisole.

14. The process as claimed in claim 13, wherein the 4-chloromethyl anisole is further converted to anisaldehyde.

* * * * *